United States Patent
Robison

(10) Patent No.: US 8,858,596 B2
(45) Date of Patent: Oct. 14, 2014

(54) SUTURE ANCHOR HAVING A SUTURE ENGAGING STRUCTURE

(75) Inventor: Cortny David Robison, Salt Lake City, UT (US)

(73) Assignee: Stryker Corporation, Kalamazoo, MI (US)

( * ) Notice: Subject to any disclaimer, the term of this patent is extended or adjusted under 35 U.S.C. 154(b) by 238 days.

(21) Appl. No.: 13/424,534

(22) Filed: Mar. 20, 2012

(65) Prior Publication Data

US 2013/0253581 A1    Sep. 26, 2013

(51) Int. Cl.
*A61B 17/04* (2006.01)

(52) U.S. Cl.
USPC .......................................... 606/232

(58) Field of Classification Search
USPC ................... 606/232, 233, 300–321, 103, 74; 411/395; 24/115 R
See application file for complete search history.

(56) References Cited

U.S. PATENT DOCUMENTS

| | | | |
|---|---|---|---|
| 146,023 A | 12/1873 | Russell | |
| 197,933 A | 12/1877 | Harvey | |
| 2,570,465 A | 10/1951 | Lundholm | |
| 3,233,500 A | 2/1966 | DeVellier | |
| 3,997,138 A | 12/1976 | Crock et al. | |
| 4,175,555 A | 11/1979 | Herbert | |
| 4,340,184 A | 7/1982 | Poss | |
| 4,507,817 A | 4/1985 | Staffeld | |
| 4,537,185 A | 8/1985 | Stednitz | |
| 4,632,100 A | 12/1986 | Somers et al. | |
| 4,640,271 A | 2/1987 | Lower | |
| 4,738,255 A | 4/1988 | Goble et al. | |
| 4,741,330 A | 5/1988 | Hayhurst | |
| 4,854,311 A | 8/1989 | Steffee | |
| 4,863,383 A | 9/1989 | Grafelmann | |
| 4,870,957 A | 10/1989 | Goble et al. | |
| 5,037,422 A | 8/1991 | Hayhurst et al. | |
| 5,047,030 A | 9/1991 | Draenert | |
| 5,100,417 A | 3/1992 | Cerier et al. | |
| 5,156,616 A | 10/1992 | Meadows et al. | |
| 5,224,946 A | 7/1993 | Hayhurst et al. | |
| 5,258,016 A | 11/1993 | DiPoto et al. | |
| 5,370,662 A | 12/1994 | Stone et al. | |
| 5,417,533 A | 5/1995 | Lasner | |
| 5,456,685 A | 10/1995 | Huebner | |
| 5,472,452 A | 12/1995 | Trott | |
| 5,549,633 A | 8/1996 | Evans et al. | |
| 5,571,139 A | 11/1996 | Jenkins, Jr. | |
| 5,573,548 A | 11/1996 | Nazre et al. | |
| 5,584,836 A | 12/1996 | Ballintyn et al. | |
| 5,601,557 A | 2/1997 | Hayhurst | |
| 5,601,558 A | 2/1997 | Torrie et al. | |

(Continued)

FOREIGN PATENT DOCUMENTS

| | | |
|---|---|---|
| AU | 0784963 | 11/2002 |
| CA | 2 386 621 A1 | 11/2002 |

(Continued)

*Primary Examiner* — Katrina Stransky
(74) *Attorney, Agent, or Firm* — Flynn, Thiel, Boutell & Tanis, P.C.

(57) ABSTRACT

A suture anchor for implanting in hard tissue, such as bone. The suture anchor carries thereon a suture engaging structure formed from a loop of suture material, which structure cooperates with working or repair suture associated with an inserter device so as to attach the working suture to the suture anchor to reattach soft tissue to bone.

24 Claims, 5 Drawing Sheets

(56) References Cited

U.S. PATENT DOCUMENTS

| | | | | |
|---|---|---|---|---|
| 5,628,766 | A | 5/1997 | Johnson | |
| 5,643,320 | A | 7/1997 | Lower et al. | |
| 5,647,874 | A | 7/1997 | Hayhurst | |
| D385,352 | S | 10/1997 | Bales et al. | |
| 5,690,676 | A | 11/1997 | DiPoto et al. | |
| 5,709,708 | A | 1/1998 | Thal | |
| 5,725,529 | A | 3/1998 | Nicholson et al. | |
| 5,733,307 | A | 3/1998 | Dinsdale | |
| 5,814,070 | A | 9/1998 | Borzone | |
| 5,871,486 | A | 2/1999 | Huebner et al. | |
| 5,891,146 | A | 4/1999 | Simon et al. | |
| 5,891,168 | A | 4/1999 | Thal | |
| 5,893,880 | A | 4/1999 | Egan et al. | |
| 5,911,721 | A | 6/1999 | Nicholson et al. | |
| 5,941,882 | A | 8/1999 | Jammet et al. | |
| 5,951,560 | A | 9/1999 | Simon et al. | |
| 5,957,953 | A | 9/1999 | DiPoto et al. | |
| 5,964,764 | A | 10/1999 | West, Jr. et al. | |
| 5,964,768 | A | 10/1999 | Huebner | |
| 5,964,783 | A | 10/1999 | Grafton et al. | |
| 6,030,162 | A | 2/2000 | Huebner | |
| 6,079,921 | A | 6/2000 | Gauthier et al. | |
| 6,096,060 | A | 8/2000 | Fitts et al. | |
| 6,117,162 | A | 9/2000 | Schmieding et al. | |
| 6,139,565 | A | 10/2000 | Stone et al. | |
| 6,214,031 | B1 | 4/2001 | Schmieding et al. | |
| 6,264,677 | B1 | 7/2001 | Simon et al. | |
| 6,299,615 | B1 | 10/2001 | Huebner | |
| 6,436,124 | B1 | 8/2002 | Anderson et al. | |
| 6,468,277 | B1 | 10/2002 | Justin et al. | |
| 6,511,499 | B2 | 1/2003 | Schmieding et al. | |
| 6,517,564 | B1 | 2/2003 | Grafton et al. | |
| 6,517,578 | B2 | 2/2003 | Hein | |
| 6,569,188 | B2 | 5/2003 | Grafton et al. | |
| 6,610,080 | B2 | 8/2003 | Morgan | |
| 6,616,665 | B2 | 9/2003 | Grafton et al. | |
| 6,635,074 | B2 | 10/2003 | Bartlett | |
| 6,641,597 | B2 | 11/2003 | Burkhart et al. | |
| 6,648,892 | B2 | 11/2003 | Martello | |
| 6,652,563 | B2 | 11/2003 | Dreyfuss | |
| 6,685,728 | B2 | 2/2004 | Sinnott et al. | |
| 6,726,707 | B2 | 4/2004 | Pedlick et al. | |
| 6,730,092 | B2 * | 5/2004 | Songer | 606/308 |
| 6,773,436 | B2 | 8/2004 | Donnelly et al. | |
| 6,840,953 | B2 | 1/2005 | Martinek | |
| 6,887,259 | B2 | 5/2005 | Lizardi | |
| 6,916,333 | B2 | 7/2005 | Schmieding et al. | |
| 6,923,824 | B2 | 8/2005 | Morgan et al. | |
| 7,081,126 | B2 | 7/2006 | McDevitt et al. | |
| 7,090,675 | B2 | 8/2006 | Songer | |
| 7,163,540 | B2 | 1/2007 | Martello | |
| 7,189,251 | B2 | 3/2007 | Kay | |
| 7,195,634 | B2 | 3/2007 | Schmieding et al. | |
| 7,217,279 | B2 | 5/2007 | Reese | |
| 7,226,469 | B2 | 6/2007 | Benavitz et al. | |
| 7,232,455 | B2 | 6/2007 | Pedlick et al. | |
| 7,309,337 | B2 | 12/2007 | Colleran | |
| 7,322,978 | B2 | 1/2008 | West, Jr. | |
| 7,500,983 | B1 | 3/2009 | Kaiser et al. | |
| 7,530,990 | B2 | 5/2009 | Perriello et al. | |
| 7,588,587 | B2 | 9/2009 | Barbieri et al. | |
| 7,611,521 | B2 | 11/2009 | Lubbers et al. | |
| 7,678,134 | B2 | 3/2010 | Schmieding et al. | |
| 7,695,495 | B2 | 4/2010 | Dreyfuss | |
| 7,780,701 | B1 | 8/2010 | Meridew et al. | |
| 7,828,820 | B2 | 11/2010 | Stone et al. | |
| 7,846,180 | B2 | 12/2010 | Cerier | |
| 7,862,585 | B2 | 1/2011 | Li et al. | |
| 7,883,528 | B2 | 2/2011 | Grafton et al. | |
| 7,883,529 | B2 | 2/2011 | Sinnott et al. | |
| 7,909,851 | B2 | 3/2011 | Stone et al. | |
| 8,029,536 | B2 | 10/2011 | Sorenson | |
| 8,114,127 | B2 | 2/2012 | West, Jr. | |
| 8,114,128 | B2 | 2/2012 | Cauldwell et al. | |
| 8,197,511 | B2 * | 6/2012 | Miller et al. | 606/232 |
| 8,439,946 | B2 * | 5/2013 | Miller et al. | 606/232 |
| 8,545,536 | B2 * | 10/2013 | Mayer et al. | 606/232 |
| 2002/0173822 | A1 | 11/2002 | Justin et al. | |
| 2003/0171778 | A1 | 9/2003 | Lizardi | |
| 2004/0093030 | A1 | 5/2004 | Cox et al. | |
| 2004/0106950 | A1 | 6/2004 | Grafton et al. | |
| 2004/0153103 | A1 | 8/2004 | Schwartz | |
| 2004/0167576 | A1 | 8/2004 | Pedlick et al. | |
| 2004/0172062 | A1 | 9/2004 | Burkhart | |
| 2004/0254580 | A1 | 12/2004 | Boock et al. | |
| 2005/0075636 | A1 | 4/2005 | Gotzen | |
| 2005/0222618 | A1 | 10/2005 | Dreyfuss et al. | |
| 2005/0222619 | A1 | 10/2005 | Dreyfuss et al. | |
| 2005/0245932 | A1 | 11/2005 | Fanton et al. | |
| 2005/0267479 | A1 | 12/2005 | Morgan et al. | |
| 2006/0161159 | A1 | 7/2006 | Dreyfuss et al. | |
| 2006/0189993 | A1 | 8/2006 | Stone | |
| 2006/0190042 | A1 | 8/2006 | Stone et al. | |
| 2006/0293675 | A1 | 12/2006 | Li et al. | |
| 2007/0005069 | A1 | 1/2007 | Contiliano et al. | |
| 2007/0032792 | A1 | 2/2007 | Collin | |
| 2007/0060922 | A1 | 3/2007 | Dreyfuss | |
| 2007/0073299 | A1 | 3/2007 | Dreyfuss et al. | |
| 2007/0142836 | A1 | 6/2007 | Schmieding et al. | |
| 2007/0142837 | A1 | 6/2007 | Dreyfuss | |
| 2007/0173845 | A1 | 7/2007 | Kim | |
| 2007/0185494 | A1 | 8/2007 | Reese | |
| 2007/0219557 | A1 | 9/2007 | Bourque et al. | |
| 2007/0219558 | A1 | 9/2007 | Deutsch | |
| 2008/0009904 | A1 | 1/2008 | Bourque et al. | |
| 2008/0167660 | A1 | 7/2008 | Moreau et al. | |
| 2008/0306510 | A1 | 12/2008 | Stchur | |
| 2009/0082807 | A1 | 3/2009 | Miller et al. | |
| 2009/0234387 | A1 * | 9/2009 | Miller et al. | 606/232 |
| 2010/0094355 | A1 | 4/2010 | Trenhaile | |
| 2010/0100127 | A1 | 4/2010 | Trenhaile | |
| 2010/0152773 | A1 | 6/2010 | Lunn | |
| 2011/0054526 | A1 | 3/2011 | Stone | |
| 2011/0224727 | A1 | 9/2011 | Housman | |
| 2012/0095506 | A1 * | 4/2012 | Mayer et al. | 606/232 |
| 2012/0197296 | A1 * | 8/2012 | Mayer et al. | 606/232 |

FOREIGN PATENT DOCUMENTS

| | | |
|---|---|---|
| EP | 1 260 182 A2 | 11/2002 |
| EP | 1 300 115 A1 | 4/2003 |
| EP | 1 486 171 A1 | 12/2004 |
| EP | 1 530 951 A2 | 5/2005 |
| EP | 1 762 187 A1 | 3/2007 |
| EP | 1 797 827 A1 | 6/2007 |
| FR | 2 254 298 | 11/1975 |
| FR | 02 588 332 | 4/1987 |
| JP | 2003010198 A1 | 1/2003 |
| SU | 01034734 | 8/1983 |

* cited by examiner

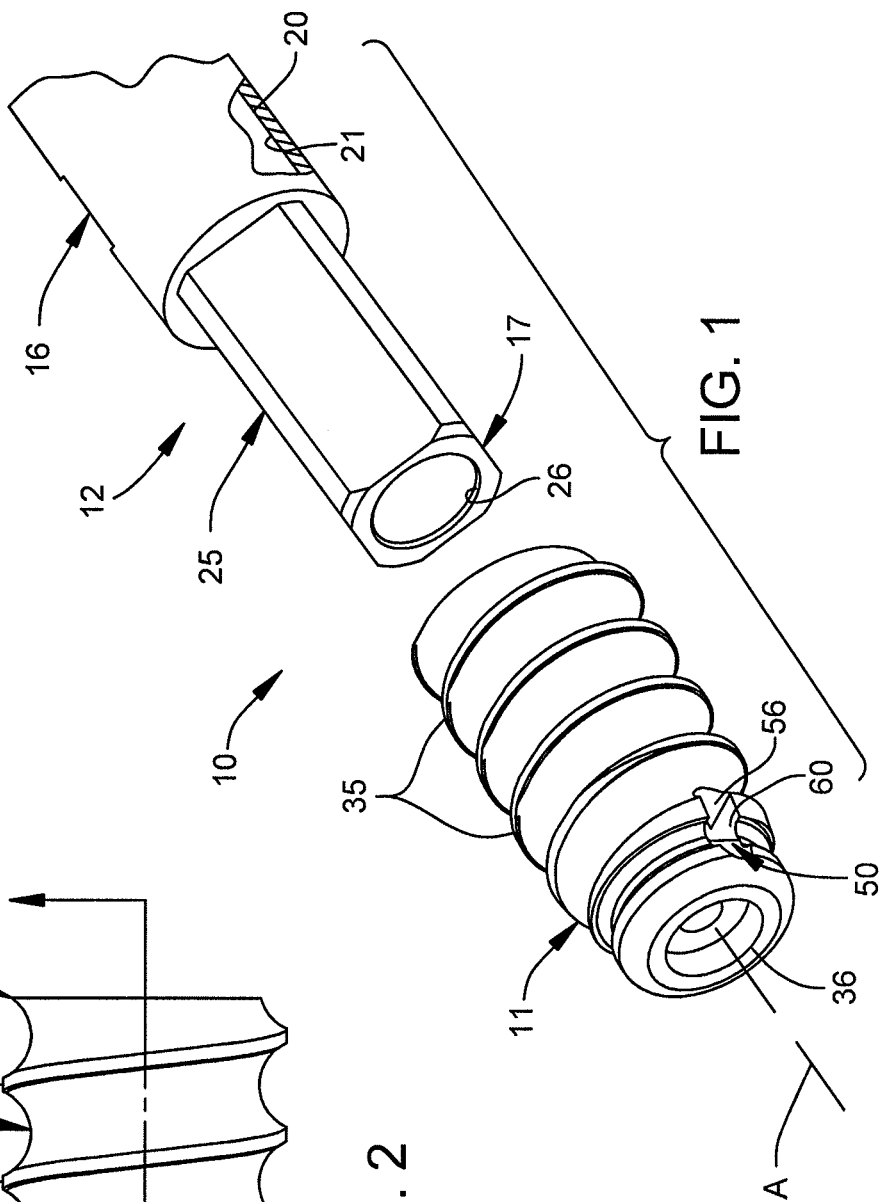
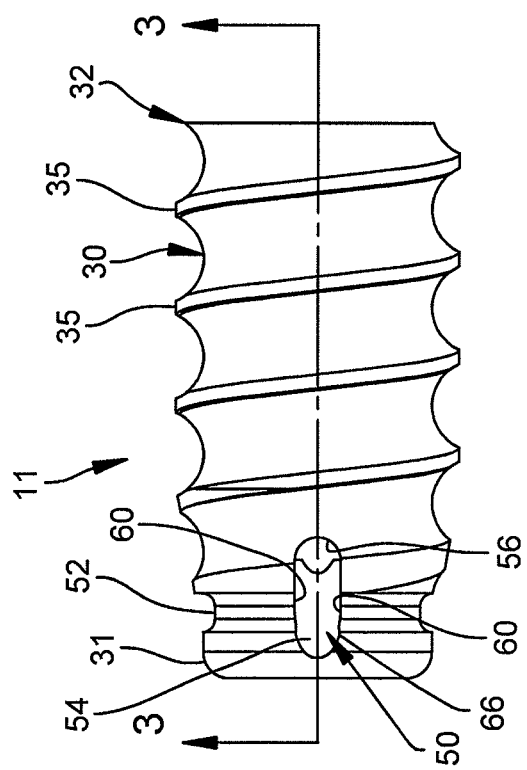

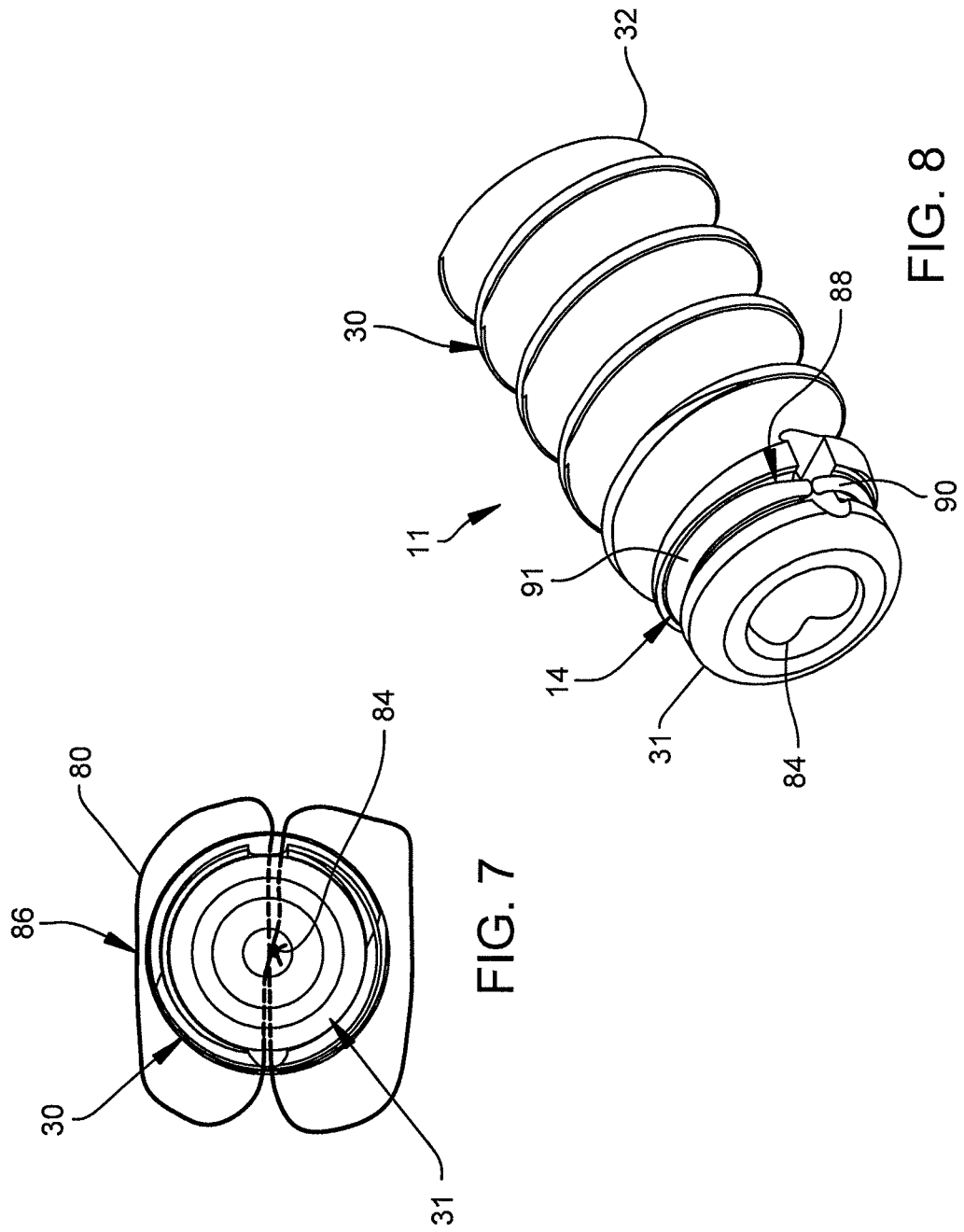

SUTURE ANCHOR HAVING A SUTURE ENGAGING STRUCTURE

FIELD OF THE INVENTION

This invention relates to a suture anchor for use in reattaching soft tissue to hard tissue.

BACKGROUND OF THE INVENTION

During some injuries, soft tissue, such as tendons or ligaments, can tear away from hard tissue, such as bone. Accordingly, it becomes necessary to reattach the soft tissue to the bone in order to facilitate the healing process. Various types of devices are used to reattach tissue, such as screws, staples and suture anchors. The instant invention relates to this latter type of attachment device.

Suture anchors may be inserted into a preformed hole made in the hard tissue, while other anchors are self-tapping. The anchors typically include an eyelet or other structure through which lengths of repair suture or working suture are threaded, which working suture is inserted simultaneously with the anchor into the hard tissue. In this regard, in some anchors, the eyelet is disposed exteriorly on the anchor, for example adjacent to or even forming part of a drive head located on the proximal end of the anchor, and in other anchors is formed interiorly within a bore defined inside the anchor. The eyelet may be formed from suture material, as disclosed in U.S. Pat. No. 6 641 597, and in other instances is formed as a rigid and integral component of the anchor body, as disclosed in U.S. Pat. No. 5 584 836. A further suture-engaging structure is disclosed in U.S. Patent Publication No. 2005/0222618, wherein the anchor incorporates a rigid pin disposed transversely across an interior bore defined in the anchor. In this variation, the working sutures are inserted into the proximal end of the anchor bore and looped over the pin to secure the suture to the anchor.

An inserter device or driver may be utilized in conjunction with the anchor to install or drive same into hard tissue and may carry working sutures thereon. For the purpose of providing pull-out resistance once the anchor is installed, some anchors are exteriorly threaded, while others are ribbed or barbed to provide appropriate pull-out resistance.

It has been discovered that increasing the biological integration of the suture anchor with the bone in which the anchor is implanted can reduce rejection potential and speed healing. In this regard, one embodiment of a suture anchor according to the invention is hollow and includes a continuous through-bore, so that the tip or distal end of the anchor, which is embedded in the bone tissue, is open, allowing the permeation/migration of blood, bone marrow, and their components (including platelets and messenchymal stem cells) into the repair site. Such permeation of blood into the through-bore leads to the formation of a blood clot which provides a matrix for tissue growth and releases cytokines and other factors that induce tissue regeneration. Additionally, the anchor may be formed of a bio-absorbable material, which also enhances healing and integration of the suture and anchor into the bone tissue.

The suture anchor according to the invention includes an anchor body having a distal end configured for insertion into hard tissue and a proximal end spaced from the distal end. The anchor body carries thereon a suture engagement structure which cooperates with working suture to attach same to the suture anchor. The suture-engaging structure may, according to one embodiment, be defined by suture material, and may be formed as a continuous loop of suture material having a portion thereof located interiorly of the anchor, such that the working suture is looped over this interior portion of the suture loop to engage the working suture with the anchor.

The suture anchor according to the invention is configured for cooperation with an inserter or driver device. The inserter device includes a handle for manipulating the device and an inserter shaft which supports the suture anchor at the distal end thereof. The inserter device carries working sutures, which working sutures are engaged with the anchor via the suture engagement structure as discussed above, and then extend proximally either interiorly or exteriorly of the inserter device.

Additionally, the suture anchor according to the invention includes a pair of passages which extend generally transversely to the anchor axis, which passages open inwardly into the anchor through-bore and outwardly through the exterior surface of the anchor. The suture-engaging structure, which may be in the form of a loop of suture material as discussed above, extends through these passages which effectively secures the structure to the anchor. In one embodiment, the loop of suture material is knotted and the knot located distally. The knot may be located completely within the bore or only partially within the bore such that a portion of the knot projects distally from the distal end of the suture anchor. The anchor body defines a surface adjacent the knot at the distal end which serves to fix the knot axially in position at the distal end of the anchor when same is loaded with force.

One possible use of the arrangement is in arthroscopic shoulder surgery, wherein the dislocation of soft tissue relative to the bone is a fairly common injury. However, this arrangement may also be utilized for the repair of small joints, such as the elbow, wrist, ankle, hand or foot. The arrangement may additionally be used to reattach small ligaments in the knee or the labrum in the hip.

BRIEF DESCRIPTION OF THE DRAWINGS

FIG. 1 is a fragmentary, partially exploded perspective view of a suture anchor and inserter arrangement according to the invention.

FIG. 2 is a plan view of the suture anchor of FIG. 1.

FIGS. 5-7 are distal end views of the suture anchor of FIGS. 1-4, showing assembly of the suture engaging structure to the anchor body.

FIG. 8 is a perspective view of the suture anchor of FIGS. 1-7, showing the suture engaging structure secured to, and in position on, the anchor body.

Figure 6:
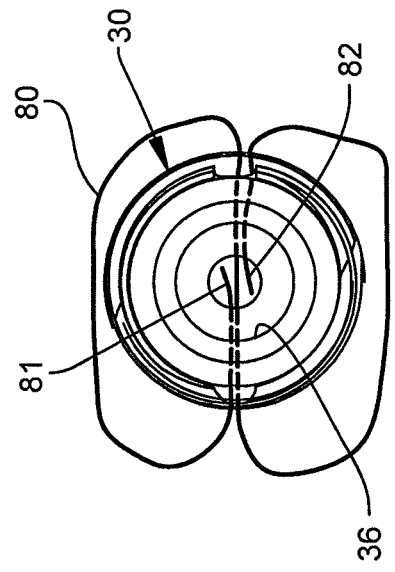
Figure 4:
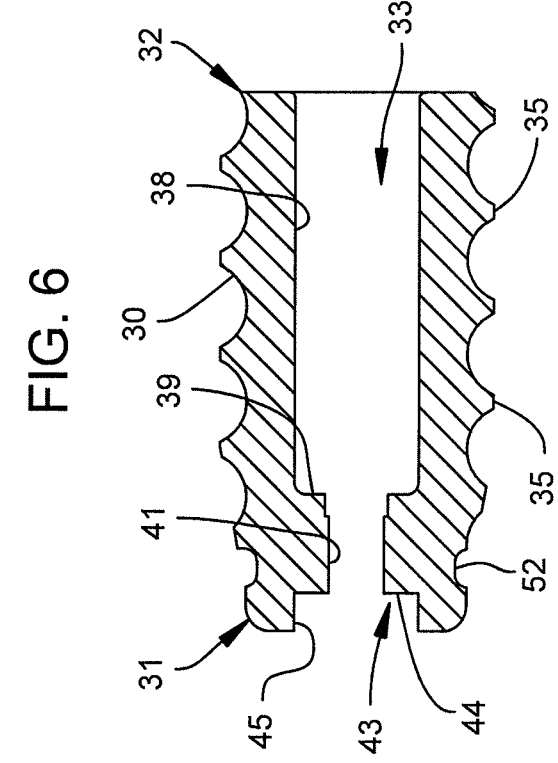
FIG. 4 is a further cross-sectional view of the suture anchor which is rotated approximately 45 degrees from the view shown in FIG. 3.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center and designated parts of thereof. The word "distally" will refer to the direction towards the end of the arrangement located closest to the patient, and the word "proximally" will refer to the direction towards the end of the arrangement located remote from the patient. Said terminology will include the words specifically mentioned, derivatives thereof, and words of similar import.

DETAILED DESCRIPTION

Referring to FIGS. 1-3 and 8, a suture anchor and inserter arrangement 10 is illustrated which is generally elongated in shape and defines a central longitudinal axis "A". The arrangement 10 generally includes a suture anchor 11 initially supported on an inserter device 12. Working or repair sutures 13 extend through the inserter device 12 and cooperate with a suture engaging structure 14 carried on the suture anchor 11.

The inserter device 12 is defined by an elongate and rigid inserter shaft 16 having a distal end 17 which engages the suture anchor 11. The inserter device 12 is of a known construction and includes a handle (not shown) which defines the proximal end of inserter device 12, which handle may include a suitable gripping surface similar to a screwdriver for use when manipulating the arrangement 10 with the hand. One type of inserter shaft which may be utilized in accordance with the invention is disclosed in U.S. Patent Publication Nos. 2009-0234387 and 2009-0082807, the entireties of which are incorporated by reference herein. Inserter shaft 16 may also include a tubular sidewall 20 which defines a bore 21 extending throughout the longitudinal length of shaft 16. Alternatively, the inserter shaft 16 may be a solid cylindrical shaft.

The distal end 17 of the inserter shaft 16 mounts thereon a projection 25. In the illustrated embodiment, projection 25 is polygonal in configuration so as to engage with the proximal end of the suture anchor 11. In one embodiment, the projection 25 has a rectangular cross-section. Projection 25 defines therein a centrally-located bore 26 which communicates with bore 21 of inserter shaft 16. It will be appreciated that other configurations of projection 26 are within the scope of the instant invention.

Turning now to suture anchor 11 as shown in FIGS. 1-4, same includes a generally elongate anchor body 30 defining a distal end 31, which is the end first inserted into the bone, and a proximal end 32 associated with the distal end 17 of inserter shaft 16. A bore 33 centered on longitudinal axis A is defined within anchor body 30 and opens through both the proximal end 32 and the distal end 31 of anchor body 30. Anchor body 30 additionally includes externally formed helical threads 35 running the length thereof and having a generally uniform thread diameter. However, other thread configurations are within the scope of the invention, such as a double-helix. The distal end 31 of the anchor body 30 is generally rounded and tapers inwardly in the proximal to distal direction, and includes a central opening 36 which is contiguous with the central bore 33. Further, in the illustrated embodiment, distal end 31 has a generally blunt shape and is of a diameter slightly smaller than the largest diameter of the remainder of anchor body 30 located proximally of distal end 31.

The central bore 33 has a proximal bore portion 38 which extends from the proximal end 32 of the anchor body 30 to an annular end face or surface 39 of anchor body 30 located proximate of the distal end 31 and oriented transversely to the axis A, and an intermediate bore portion 41 which extends axially from end face 39 towards distal end 31 of anchor body 30 and has a lesser diameter than bore portion 38. Bore 33 additionally includes a distal bore portion 43 defined by an annular surface 44 of anchor body 30, which surface 44 faces distally and is oriented transversely to axis A, and a further annular surface 45 oriented transversely to surface 44. In the illustrated embodiment surface 45 is oriented generally parallel to axis A and perpendicular to surface 44. Distal bore portion 43 opens distally through opening 36. Proximal bore portion 38 has a cross-sectional profile which matches the external configuration of the projection 25 of the inserter device 12. Further, the projection 25 is of a length to allow for full-length insertion into proximal bore portion 38 of bore 33 of the suture anchor body 30, and in the illustrated embodiment has a rectangular profile. The projection 25 can also have other profiles, such as hexagonal, oval, or star-shaped, and remain within the scope of the invention.

A pair of passages 50 and 51 extend transversely relative to the longitudinal axis A of the anchor 11, from the intermediate bore portion 41 of the bore 33 outwardly to the exterior of the anchor body 30. The passages 50 and 51 open outwardly into a circumferential groove 52 defined in the exterior surface of the anchor body 30, which groove 52 extends around the entire circumference thereof. In the illustrated embodiment, passages 50 and 51 open outwardly at diametrically opposite positions (i.e. about 180 degrees from one another) on the exterior surface of anchor body 30.

Figure 3:
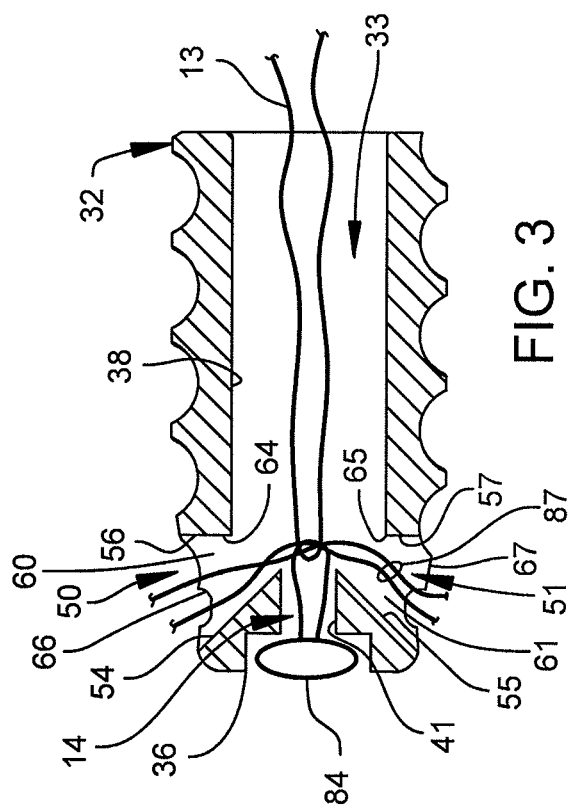
FIG. 3 is a cross-sectional view of the suture anchor, taken generally along line 3-3 of FIG. 2, and partially illustrating the suture engaging structure and working or repair suture.

As best shown in FIGS. 2 and 3, passages 50 and 51 are partially defined by respective arcuate surfaces 54 and 55 formed in the distal end 31 of anchor body 30 at an angle relative to axis A, which surfaces 54 and 55 define the distal-most extent of the respective passages 50 and 51. Specifically, each of the surfaces 54 and 55 angles upwardly as same projects away from axis A in a proximal to distal direction. In the illustrated embodiment, the radially innermost portions of surfaces 54 and 55 are oriented at an angle in the range of 10-75 degrees relative to the axis A, and for example as shown in FIG. 3 are oriented at an angle of 45 degrees relative to axis A. Passages 50 and 51 are additionally defined by respective arcuate surfaces 56 and 57 of anchor body 30 which face the respective surfaces 54 and 55 and define the most proximal extent of the respective passages 50 and 51. Surface 54 and surface 56 are connected to one another by a pair of spaced-apart side walls 60, and likewise surfaces 55 and 57 are connected to one another by spaced side walls 61. Each passage 50 and 51 opens inwardly through a respective inner opening 64 and 65, which inner openings 64 and 65 open into and communicate with intermediate bore portion 41 adjacent the junction between bore portion 41 and proximal bore portion 38. Further, each passage 50 and 51 opens outwardly through a respective outer opening 66 and 67 located at the exterior surface of anchor body 30, which openings 66, 67 in the illustrated embodiment are elongated in the direction of axis A.

Figure 5:
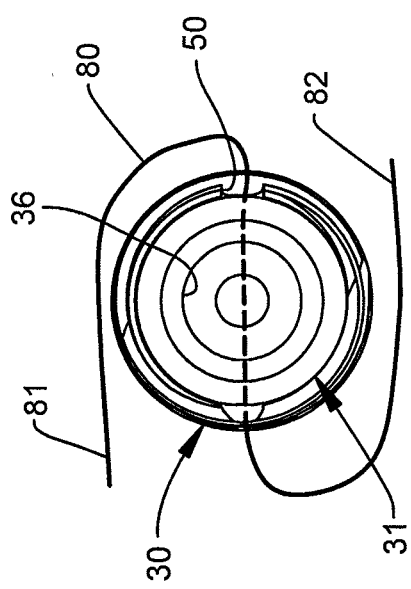

As mentioned above, suture anchor 11 carries thereon the suture engaging structure 14, which effectively serves as an attachment point for the working or repair sutures 13. In the illustrated embodiment, the suture engaging structure 14 is defined by suture material which is fixed to the anchor body 30. Specifically, and with reference to FIGS. 5-8, in order to form an eyelet for engaging the working sutures 13, a strand (or strands) of suture material 80 is passed through passages 50 and 51 so that it extends through intermediate bore portion 41 and transversely to the longitudinal axis A of the anchor body 30, and each end 81 and 82 of the suture material 80 is drawn about 180 degrees around the anchor body 30 in the circumferential groove 52 (FIG. 5) and inserted through the respective opposite passage 50, 51 back into bore portion 41 (FIG. 6). The ends 81, 82 are then drawn outwardly through the opening 36 in the distal end 31 of the anchor body 30 and secured to one another, such as by a knot 84 (FIG. 7). In one embodiment, adhesive may be utilized to reinforce and further secure knot 84. In this regard, various types of biocompatible adhesives which may be utilized to secure knot 84 are cyanoacrylates, such as Histoacryl (an n-butyl cyanoacrylate distributed by TissueSeal LLC), ethyl cyanoacrylate, butyl cianoacrylate, and octyl cyanoacrylate. Polycaprolactone (PCL), Poly-L-lactide acid (PLLA), and polyglycolic acid (PGA) may also be utilized.

Knot 84 and the diameter of intermediate bore portion 41 are of a size such that knot 84 substantially seats within distal bore portion 43, and surface or shoulder 44 effectively prevents movement of the knot 84 in the proximal direction through bore portion 38. In this regard, the knot 84 may be of a size which causes same to project outwardly somewhat from distal end 31 of anchor body 30, or may be in its entirety located completely within distal bore portion 36. The suture material thus forms a closed loop 86 having an interior section 87 (FIG. 3) located interiorly of the anchor body 30 and an exterior section 88 (FIG. 8) located exteriorly of the anchor body 30. In this regard, exterior section 88 includes two exterior segments 90 and 91 which extend in opposite directions from one another circumferentially about anchor body 30 between passages 50 and 51 within and along groove 52. Loop 86 thus defines a non-rigid or soft eyelet structure which is fixed to anchor body 30 and utilized to define an attachment point for the working suture 13 as discussed below.

One method of assembling the suture anchor 11 onto the inserter device 12 is as follows. The working suture 13 is loaded into inserter device 12, and free ends of two separate working sutures 13 (only one of which is shown in FIG. 3 for simplicity) are drawn out from bore 26. The free ends of working suture 13 are then drawn through the proximal bore portion 38 of the suture anchor 11 to capture at least one of the three "passes" of the suture material 80 which define the interior section 87 of loop 86, as shown in FIG. 3. In a preferred embodiment, working sutures 13 capture or are looped over a segment of suture material 80 proximate end 81, a central segment of suture material 80 located between ends 81 and 82, and a segment of suture material 80 proximate end 82. In this embodiment, the working sutures 13 each engage with all three passes of the suture material 80 located proximally of knot 84 as shown in FIG. 3. As tension is placed on the loop 86 by the working suture 13, the knot 84 is drawn proximally against surface 44, and the interior section 87 of loop 86 is drawn into bore portion 38 of the central bore 33. The free ends of the working sutures 13 are then drawn back through the central bore 26 of the inserter device 12. It will be appreciated that, instead of utilizing two pairs of working sutures 13, a single working suture could be engaged with suture loop 86. Three or more working sutures could also be utilized.

The bore 38 which opens at the proximal end of anchor 11 is circumferentially or rotationally aligned with the projection 25 of inserter device 12 at the distal end 17 of inserter shaft 16, and the projection 25 is inserted into the proximal bore portion 38 of the suture anchor 11 until the projection 25 extends the full depth of the bore portion 38 to end face 39 of anchor body 30. The projection 25 thereby fully supports the length of the suture anchor 11, and increases the bearing surface between the projection 25 and the central bore 33 of the suture anchor 11. A given force is necessary to drive the suture anchor 11 into bone, and the increased bearing surface between the projection 25 and the suture anchor 11 distributes this force over a greater area, thereby diminishing the shearing force exerted on the material of the anchor body 30. The projection 25 further provides full length support of the hollow suture anchor 11 to prevent its collapse during insertion into bone. In the illustrated embodiment, the anchor 11 is not self-tapping, and thus requires a pilot hole be prepared in the bone before insertion. The free ends of the working sutures 13 located adjacent the handle of the inserter device 12 are then pulled in a proximal direction so as to tension the working sutures 13 and are then secured to the inserter device 12 to maintain the sutures 13 in a fixed position relative to inserter device 12.

It will be appreciated that suture loop 86 may be defined by a single strand of suture material, double or triple strands. In this regard, it may be desirable to use a single strand of suture material to form loop 86 if such material has sufficient strength, so as to simplify assembly, minimize materials, and reduce the volume of suture material within anchor body 30. Also, it may be desirable to use triple strands if the suture material utilized has a smaller diameter but is not of sufficient strength such that additional strands are necessary.

Figure 9:
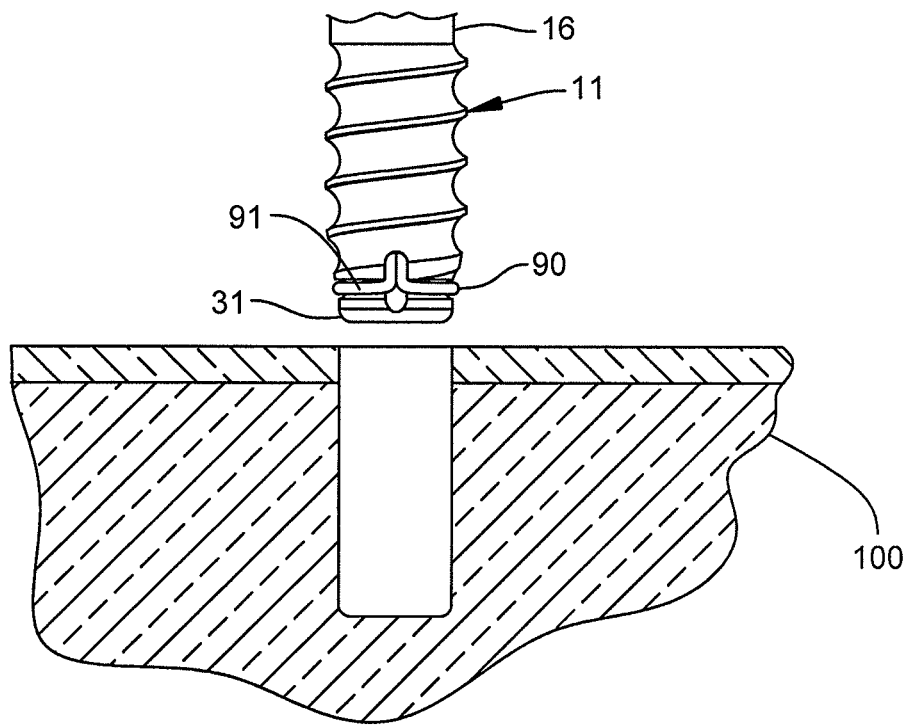
FIG. 9 is a fragmentary view illustrating the suture anchor being installed within a bone using the inserter device.
Figure 10:
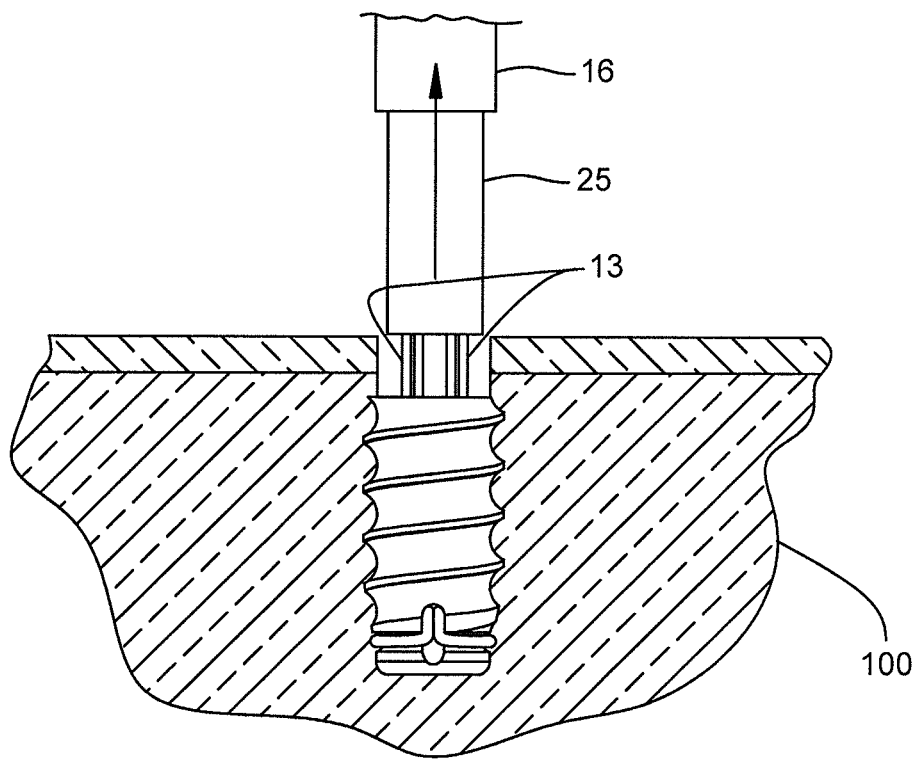
FIG. 10 is a fragmentary view illustrating the inserter device being pulled away from the suture anchor.

The suture anchor 11 is intended for implanting within hard tissue, such as bone 100. One method of implanting anchor 11 will be described with reference to FIGS. 9-12. A hole is pre-formed in the bone 100 with a tap instrument. In this regard, the tap instrument has a pointed tip which initially punches through the bone 100, and is threaded along its length. The tap instrument is thus rotated relative to the bone so that a pre-formed threaded hole is defined in the bone 100. The distal end 31 of the anchor 11 is then aligned with this hole (FIG. 9), and the anchor 11 (installed on the inserter device 12 as discussed above) is rotatably driven into the bone 10 (FIG. 10). Once the anchor 11 is located at the desired depth within the bone 100, the inserter device 12 is pulled in a proximal direction away from the anchor 11 (FIG. 10) to unseat the anchor 11 therefrom. In this regard, the working sutures 13 would be released from their securement with the inserter device 12 prior to the aforementioned step, so as to allow working sutures 13 to move freely relative to the inserter device 12 as the anchor 11 is deployed therefrom. Continued movement of the inserter device 12 in a proximal direction frees the working sutures 13 from the device 12, so that the surgeon can use the sutures 13 to anchor soft tissue 101 to the bone 100.

Figure 11:
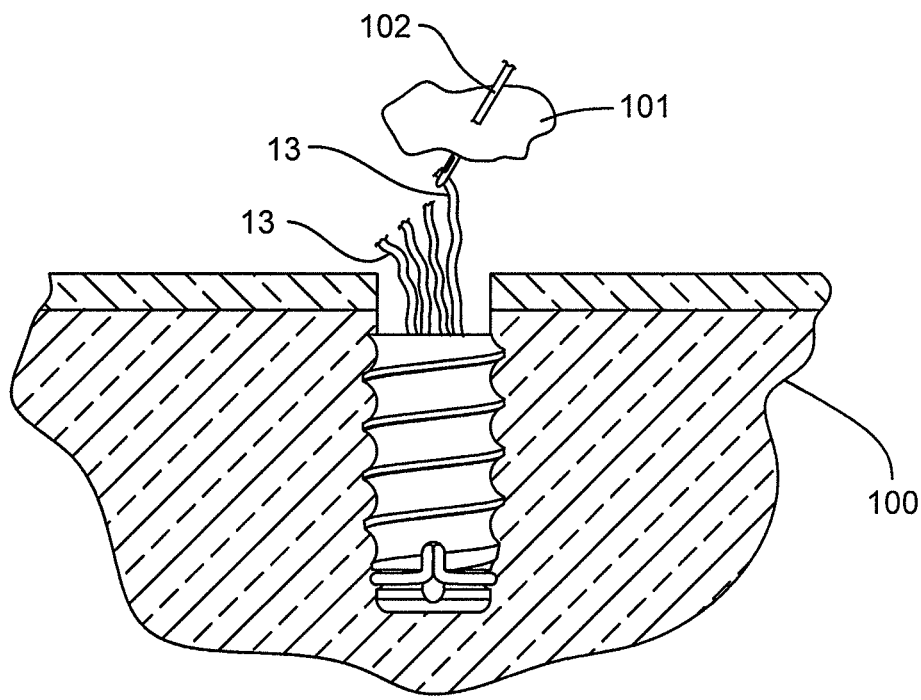
FIG. 11 is a fragmentary view illustrating the attachment of the working suture to soft tissue.

As shown in FIG. 11, the surgeon utilizes a suitable surgical tool 102 to grasp one of the working sutures 13 and pull same through the soft tissue 101. The same step is performed with the opposite working suture 13. The two free ends of each of the working sutures 13 now extend around and through a portion of the soft tissue 101, and the surgeon forms sliding knots 103 in the working sutures 13. The knots 103 are moved down the working suture 13 to cinch the soft tissue 101 against the bone 100 at the location of anchor 11 (FIG. 12).

The arrangement as discussed above includes the projection 25 on the distal end 17 of inserter device 12 which cooperates with the proximally-opening bore 38 of the suture anchor 11. It will be appreciated that this configuration could be reversed, for example, the suture anchor 11 could include a projection or external drive head which engages within a corresponding recess formed in the distal end 17 of the inserter device 12. However, forming the anchor 11 with an internal construction for allowing cooperation with the inserter device 12 is believed advantageous as compared to conventional anchors which include externally projecting drive heads at their proximal ends. In this regard, configuring the anchor in this manner allows same to be made smaller, so as to cause less trauma to the patient, and also allows the anchor to be provided with a greater thread length within the available anchor length, and thus is believed to result in a better engagement of the anchor within the bone.

Figure 12:
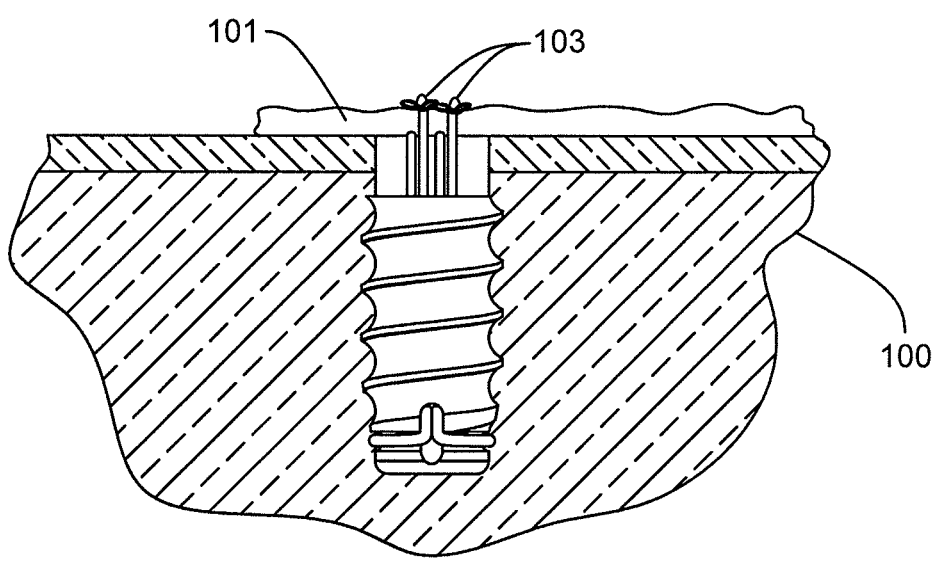
FIG. 12 is a fragmentary view illustrating the soft tissue fully attached to the bone.

As shown in FIG. 12, the anchor 11 serves as the attachment point of the soft tissue 101 to the bone 100, and thus the design of the anchor should maximize pull-out resistance as much as possible. When the tissue 101 exerts an outward force on the anchor 11 (such as when a muscle is flexed), the anchor 11 must as much as possible resist this force and remain in place within the bone 100. In this regard, the placement of the loop segments 90 and 91 of loop 86 exteriorly and circumferentially around the anchor body 30 cause an inward contracting force on the anchor 11 when loaded with force in a proximal direction. Also during loading of the anchor 11, the knot 84 bears against surface 44 at the distal end of the anchor body 30. The force generated by knot 84 thus tends to exert an outward force on anchor body 30, which effectively counteracts the inward contracting force exerted by the exterior loop segments 90 and 91. These forces which act in opposition to one another during loading of the anchor 11 thus tend to balance one another out and help to prevent the anchor 11 from collapsing. Additionally, providing surface 44 against which the knot 84 bears during loading provides an additional load-bearing surface for the loop 86, which helps to better distribute forces on the anchor body 30. Further, the forwardly or distally angled orientation of the passages 50 and 51 at the distal end of the anchor body 30 allows the distal end 31 of the anchor 11 to be made thicker which provides improved support for loop 86, helps to distribute force-load and improves pull-out resistance. Additionally, the thick distal end 31 allows the anchor, if desirable, to be made of softer materials which are more easily absorbed by the body when the anchor 11 is constructed of bio-absorbable material.

The suture anchor 11 according to the invention may be constructed of any suitable bio-absorbable material or non-absorbable material. In the preferred embodiment of the invention, the anchor 11 is constructed of bio-absorbable material. An example of a bio-absorbable material which may be utilized is BIOSTEON® (HA/PLLA), which is an absorbable polymer manufactured by Biocomposites Ltd. PLLA, which is a bio-absorbable plastic, may also be utilized. Alternatively, the anchor may be constructed of non-absorbable plastic, such as PEEK, or non-absorbable metal, such as titanium. It will be appreciated that other types of materials may be utilized in accordance with the invention, and the above are presented only as examples.

The suture anchor 11 may have a length dimension of about 10.8 mm, and may have an outside diameter of about 4.5mm, 5.5mm or 6.5mm. These dimensions are presented only as an example of relative dimensions of anchor 11, and are not intended to be limiting.

The inserter device 12 discussed above includes projection 25 at distal end 17 thereof. The shaft 16 and projection 25 of the inserter device 12 include centrally located bores 21 and 26 through which working sutures 13 are passed, as described above. In the alternative, suture anchor arrangements are known which integrate a suture/needle combination. The common curved needle configuration precludes passage of the suture through a cannulated inserter device, such as device 12. Therefore, a non-cannulated inserter or a partially cannulated inserter (not shown) in such an application would be compatible for use with the suture anchor 11, with the working suture 13 passing over the exterior surface of the inserter device.

Although a particular preferred embodiment has been disclosed in detail for illustrative purposes, it will be recognized that variations or modifications of the disclosed apparatus, including the rearrangement of parts, lie within the scope of the present invention.

What is claimed is:

1. A suture anchor arrangement comprising:
a suture anchor including an anchor body defining a longitudinal axis, said anchor body having a distal end for insertion into bodily tissue and a proximal end spaced axially from said distal end, said anchor body defining therein a substantially axially-extending bore disposed within an interior of said anchor body, said bore opening outwardly through said distal end to form a distal bore portion and opening outwardly through said proximal end to form a proximal bore portion, and a pair of passages extending through said distal end of said anchor body, each said passage having an inner end which opens into said bore and an outer end which opens through an exterior of said anchor body, said outer ends of the respective said passages being circumferentially spaced from one another along said exterior of said anchor body, each said passage having a passage surface which angles in a direction towards a terminal distalmost end of said distal end and away from said proximal end of said anchor body as said passage projects from adjacent the respective said inner end towards the respective said outer end, said passage surface at said inner end of the respective said passage being located at a greater axial distance from said distalmost end of said distal end of said anchor body than said passage surface at said outer end of the respective said passage, said anchor body having a surface oriented transversely to the axis which defines part of said distal bore portion;
a length of working suture for securing soft tissue to said anchor body; and
a length of suture material distinct from said working suture, said suture material having a pair of respective free terminal ends which are secured to one another to form a knot such that said suture material forms a closed and continuous loop of suture material which extends through said passages of said anchor body to secure said suture material to said anchor body, said loop having an interior loop portion disposed within said bore and extending between the respective said inner ends of said passages and a pair of exterior loop portions, said exterior loop portions extending circumferentially along said exterior of said anchor body in opposite directions from one another and along diametrically opposite sides of said exterior, each said exterior loop portion extending from said outer end of one of said passages to said outer end of the other said passage, said knot being disposed in said distal bore portion adjacent said surface.

2. The arrangement of claim 1, wherein each said exterior loop portion extends through said passages and encircles a portion of said anchor body.

3. The arrangement of claim 1, wherein said knot is disposed to abut said surface in said distal bore portion when said anchor is loaded with force in a proximal direction, said surface being disposed to prevent movement of said knot in a proximal direction.

4. The arrangement of claim 3, wherein said inner ends of said passages are disposed axially adjacent said distal bore portion.

5. The arrangement of claim 4, wherein said bore includes an intermediate bore portion disposed axially between said proximal and distal bore portions, said intermediate bore portion having a diameter which is less than a diameter of said distal bore portion, and said surface defines part of said distal bore portion and extends substantially radially between and interconnects said distal bore portion and said intermediate bore portion.

6. The arrangement of claim 5, wherein the diameter of said intermediate bore portion is less than a diameter of said proximal bore portion.

7. The arrangement of claim 5, wherein said inner ends of said passages are disposed immediately axially adjacent said intermediate bore portion.

8. A suture anchor arrangement comprising a suture anchor including an anchor body defining a longitudinal axis, a distal end for insertion into bodily tissue and a proximal end spaced axially therefrom, said anchor body having a hollow interior defined by an axially extending bore extending continuously from said proximal end to said distal end, a pair of passages disposed adjacent said distal end of said anchor body, each said passage having an inner end opening into said bore within said hollow interior and an outer end opening at an exterior surface of said anchor body, and a suture retention interface disposed within said hollow interior and defining an attachment location for repair suture utilized to secure soft tissue to bone, said suture retention interface including a loop extending through said passages so as to encircle a portion of said anchor body, said loop having a pair of exterior loop parts extending between said passages outside said bore and circumferentially along opposite sides of said exterior surface of said anchor body and an interior loop part connected to said exterior loop parts and extending between said passages within said hollow interior in a direction transverse to the axis for attachment to repair suture, said loop having a pair of free ends secured to one another to form a knot, said knot being disposed in said distal end of said anchor within said bore, said anchor body defining a surface within said distal end oriented transversely to the axis and disposed immediately adjacent said knot to prevent said knot from moving in a proximal direction axially beyond said surface during loading of said anchor.

9. The arrangement of claim 8, wherein each said passage angles in a direction towards a terminal distalmost part of said distal end of said anchor body as said passage projects from adjacent the respective said inner end towards the respective said outer end.

10. The arrangement of claim 8, wherein said loop is a closed and continuous loop of suture material.

11. The arrangement of claim 8, wherein said surface of said anchor body defines a portion of said bore at said distal end of said anchor, said surface being annular in configuration and facing towards a terminal distalmost part of said distal end of said anchor body, said surface abutting said knot during loading of said anchor to prevent said knot from moving in a proximal direction axially beyond said surface.

12. The arrangement of claim 11, further including a length of repair suture attached to said interior loop part within said bore.

13. A suture anchor arrangement comprising a suture anchor including an anchor body defining a longitudinal axis, said anchor body having a leading distal end for insertion into bodily tissue and a trailing proximal end spaced axially from said distal end, said anchor body defining therein a bore disposed within an interior of said anchor body, said bore opening outwardly through said leading distal end and outwardly through said trailing proximal end, a pair of passages extending through said anchor body at said leading distal end, each said passage having an inner end which opens into said bore and an outer end which opens through an exterior surface of said anchor body, said outer ends of the respective said passages being spaced from one another along said exterior surface of said anchor body, each said passage extending angularly relative to the axis in a direction away from said trailing proximal end of said anchor body and in a direction towards a terminal distalmost part of said leading distal end of said anchor body as said passage projects from adjacent the respective said inner end towards the respective said outer end, a length of repair suture, an attachment structure defining an attachment location for securing of said repair suture to said anchor body, said attachment structure including a loop of suture material extending through said passages and having an interior portion disposed within said bore and an exterior portion extending along said exterior surface of said anchor body.

14. The arrangement of claim 13, wherein said loop comprises a closed and continuous loop of suture material, and said exterior portion includes a pair of exterior segments of said loop which extend in opposite directions from one another circumferentially along said exterior surface of said anchor.

15. The arrangement of claim 14, wherein said interior portion includes an interior segment of said loop which extends transversely relative to the axis across said bore and defines said attachment location for said repair suture.

16. The arrangement of claim 15, wherein said repair suture is distinct from said suture material of said loop, said repair suture extending into said bore and engaging with said interior segment of said loop to secure said repair suture to said anchor body.

17. The arrangement of claim 14, wherein said loop includes a knot disposed in said bore within said distal end of said anchor, said anchor body defining a shoulder located within said bore axially adjacent said knot, said shoulder being disposed to prevent movement of said knot in a proximal direction during loading of said anchor.

18. The arrangement of claim 17, wherein said bore includes a distal bore portion disposed within said distal end of said anchor in which said knot is disposed and a proximal bore portion disposed proximally of said distal bore portion, said distal bore portion having a transverse dimension which is greater than a transverse dimension of said proximal bore portion, said shoulder extending substantially radially between said distal and proximal bore portions.

19. The arrangement of claim 17, wherein each said exterior segment of said loop extends through said passages so as to encircle a portion of said anchor body.

20. The arrangement of claim 19, wherein said shoulder is annular in configuration and faces distally.

21. The arrangement of claim 3, wherein said surface faces away from said proximal bore portion and towards said terminal distalmost end of said distal end, said surface being disposed to prevent movement of said knot in a proximal direction axially beyond said surface during loading of said anchor.

22. The arrangement of claim 11, wherein said portion of said bore opens axially through said distal end of said anchor body, said distal end of said anchor body having an annular surface oriented substantially parallel to the axis and facing away from said exterior surface of said anchor body, said annular surface and said surface adjoining one another and being oriented transversely to one another, said annular surface and said surface together defining said portion of said bore in which said knot is disposed.

23. The arrangement of claim 13, wherein said loop of suture material includes a knot disposed in said bore within said distal end of said anchor, said anchor body defining a shoulder located within said bore axially adjacent said knot, said shoulder being annular in configuration and oriented transversely to the axis, said shoulder being disposed to face towards said knot to prevent movement of said knot in a proximal direction during loading of said anchor.

24. The arrangement of claim 1, wherein said working suture engages with said interior loop portion to secure said working suture to said anchor body.

* * * * *